(12) United States Patent
Kourai et al.

(10) Patent No.: US 7,176,276 B2
(45) Date of Patent: Feb. 13, 2007

(54) ANTIMICROBIAL PEPTIDE AND USE THEREOF

(75) Inventors: Hiroki Kourai, 230-2, Tomiyoshi, Kawauchi-cho, Tokushima-shi, Tokushima (JP) 771-0112; Takuya Maeda, Tokushima (JP); Hideaki Nagamune, Tokushima (JP); Nahoko Kobayashi, Tokushima (JP)

(73) Assignees: Toagosei Co., Ltd., Tokyo (JP); Hiroki Kourai, Tokushima (JP)

( * ) Notice: Subject to any disclaimer, the term of this patent is extended or adjusted under 35 U.S.C. 154(b) by 333 days.

(21) Appl. No.: 10/852,136

(22) Filed: May 25, 2004

(65) Prior Publication Data

US 2005/0171335 A1    Aug. 4, 2005

(30) Foreign Application Priority Data

Oct. 20, 2003    (JP)    ............ P. 2003-359002

(51) Int. Cl.
*C07K 4/00*    (2006.01)
(52) U.S. Cl. .................................... 530/300
(58) Field of Classification Search ............. None
See application file for complete search history.

(56) References Cited

U.S. PATENT DOCUMENTS 5,962,637 A  * 10/1999  Shone et al. ................ 530/329

OTHER PUBLICATIONS

Molecular Design of Peptide Antimicrobial Agent.

* cited by examiner

*Primary Examiner*—Cecilia J. Tsang
*Assistant Examiner*—Christina M Bradley
(74) *Attorney, Agent, or Firm*—Sughrue Mion, PLLC

(57) ABSTRACT

An object of the invention is to provide an antimicrobial peptide having an amino acid sequence which is different from a peptide existing and functioning as an antimicrobial peptide in the natural world and is not based on the conventional developmental approach for an antimicrobial peptide-containing antimicrobial agent, and a polynucleotide coding for said peptide. Another object is to provide an antimicrobial agent which contains such an antimicrobial peptide. Namely, an antimicrobial peptide represented by a general formula (1)

$$(Xa)n\text{-}S \qquad (1)$$

wherein Xa of the formula (1) is a hydrophilic amino acid residue, n is an integer of from 1 to 6, two or more of the Xa may be the same or different from one another, S is a peptide represented by hydrophobic amino acid part-basic amino acid part-bridge part-basic amino acid part-hydrophobic amino acid part, and amino acid residue of the bridge part is selected from the group consisting of hydrophobic amino acids and neutral amino acids.

3 Claims, No Drawings

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 1

Arg Leu Leu Arg Lys Trp Trp Trp Lys Arg Leu Leu
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 2

Arg Arg Leu Leu Arg Lys Trp Trp Trp Lys Arg Leu Leu
1               5                   10
```

```
<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 3

Arg Arg Arg Leu Leu Arg Lys Trp Trp Trp Lys Arg Leu Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Leu Leu Arg Lys Trp Trp Trp Lys Arg Leu Leu
1               5                   10
```

US 7,176,276 B2

ANTIMICROBIAL PEPTIDE AND USE THEREOF

FIELD OF THE INVENTION

This invention relates to an artificially designed antimicrobial peptide. Also, it relates to an antimicrobial agent or germicidal agent which contains said antimicrobial peptide.

BACKGROUND OF THE INVENTION

Since it is considered that antimicrobial peptides have broad antimicrobial spectra and hardly generate drug-resistant microorganisms, use of antimicrobial peptides is expected for the purpose of preventing and treating bacterial infectious diseases of human and animals or of adding antimicrobial property to food materials and the like articles.

A large number of antimicrobial peptides have so far been isolated from animals and plants. For example, an antimicrobial peptide derived from a Taiwanese beetle and an antimicrobial agent containing said antimicrobial peptide as the active ingredient have been disclosed (cf. Reference 1). Also, an antimicrobial peptide derived from scorpion toxin and an antimicrobial agent containing said antimicrobial peptide as the active ingredient have bee disclosed (e.g., see Reference 2).

Each of the aforementioned antimicrobial peptides contains lysine, arginine and/or histidine and the like basic amino acids and is called cationic antimicrobial peptide in which its charge as the entire peptide molecule becomes positive. It is considered that the reaction principle of these antimicrobial peptides is based on the electrostatic interaction of the positively charged basic amino acid moiety in the antimicrobial peptide with the cell surface membrane (e.g., see Reference 3).

Each of the aforementioned antimicrobial peptides described in the respective official gazettes is a result of discovering and isolating a substance originally existing as an antimicrobial peptide in the natural world (or a peptide prepared by partially modifying the amino acid sequence of a natural antimicrobial peptide). Thus, so far as a peptide originally existing as an antimicrobial peptide is used as the main component, it is difficult in general to develop an antimicrobial agent having the antimicrobial performance superior to the antimicrobial activity and antimicrobial spectrum originally exerted by the peptide in the natural world.

Reference 1 JP-A-2000-063400 official gazette
Reference 2 JP-A-2001-186887 official gazette
Reference 3 M. Zasloff. Nature, vol. 415. pp. 389–395, 2002

SUMMARY OF THE INVENTION

An object of the invention is to provide an antimicrobial peptide having an amino acid sequence which is not restricted to a peptide existing and functioning as an antimicrobial peptide in the natural world and is not based on the conventional developmental approach for an antimicrobial peptide-containing antimicrobial agent, and a polynucleotide coding for said peptide. Another object of the invention is to provide an antimicrobial agent and the like, which contain such an antimicrobial peptide.

As a result of carrying out intensive studies, the present inventors have found that an antimicrobial peptide represented by a general formula (1) can further improve antimicrobial properties than those of the S moiety of the general formula (1), thus resulting in the accomplishment of the invention.

That is, the invention includes the following embodiments.

(1) An antimicrobial peptide represented by a general formula (1)

$$(Xa)n-S \qquad (1)$$

wherein Xa of the formula (1) is a hydrophilic amino acid residue, n is an integer of from 1 to 6, two or more of the Xa may be the same or different from one another, S is a peptide represented by hydrophobic amino acid part-basic amino acid part-bridge part-basic amino acid part-hydrophobic amino acid part, and amino acid residue of the bridge part is selected from the group consisting of hydrophobic amino acids and neutral amino acids.

(2) The antimicrobial peptide described in the aforementioned (1), wherein the hydrophilic amino acid constituting the Xa is respectively and independently selected from arginine, lysine, histidine, aspartic acid, glutamic acid, asparagine and glutamine.

(3) The antimicrobial peptide described in the aforementioned (1), wherein the number of amino acid residues of the hydrophobic amino acid part existing at two positions may be the same or different from each other, and each is an integer of from 2 to 6.

(4) The antimicrobial peptide described in the aforementioned (1), wherein amino acids of the hydrophobic amino acid part may be the same or different from one another and are respectively selected from the group consisting of valine, leucine, isoleucine, phenylalanine, proline, glycine, alanine and methionine.

(5) The antimicrobial peptide described in the aforementioned (1), wherein the number of amino acid residues of the basic amino acid part existing at two positions may be the same or different from each other, and each is an integer of from 2 to 6.

(6) The antimicrobial peptide described in the aforementioned (1), wherein amino acids of the basic amino acid part may be the same or different from one another and are respectively selected from the group consisting of lysine, arginine and histidine.

(7) The antimicrobial peptide described in the aforementioned (1), wherein the number of amino acid residues of the bridge part is an integer of from 2 to 6.

(8) The antimicrobial peptide described in the aforementioned (1), wherein the hydrophobic amino acid and neutral amino acid of the bridge part are selected from the group consisting of valine, leucine, isoleucine, phenylalanine, tryptophan, glycine, alanine, methionine, serine, threonine, cysteine, tyrosine, asparagine and glutamine.

(9) An antimicrobial peptide which has the amino acid sequence described in SEQ ID NO:1, SEQ ID NO:2 or SEQ ID NO:3.

(10) An antimicrobial agent composition which contains the antimicrobial peptide described in any one of the aforementioned (1) to (9) and a carrier.

(11) A sterilization method which comprises the step of applying the antimicrobial peptide described in any one of the aforementioned (1) to (9).

(12) A method for inhibiting bacterial growth, which comprises the step of applying the antimicrobial peptide described in any one of the aforementioned (1) to (9).

DETAILED DESCRIPTION OF THE INVENTION

The hydrophilic amino acid of the general formula (1) is selected from arginine, lysine, histidine, aspartic acid, glutamic acid, asparagine and glutamine.

The number of amino acid residues of the hydrophobic amino acid part is from 2 to 6, amino acids of the hydrophobic amino acid part are selected from valine, leucine, isoleucine, phenylalanine, proline, glycine, alanine and methionine, amino acid residues of the hydrophobic amino acid part existing at two positions may be the same or different from one another, and the number of amino acid residues of the hydrophobic amino acid parts may be the same or different from each other.

The number of amino acid residues of the basic amino acid part of the general formula (1) is from 2 to 6, amino acid residues of the basic amino acid part existing at two positions may be the same or different from one another, and the number of amino acid residues of the basic amino acid parts may be the same or different from each other.

The number of amino acid residues of the bridge part of the general formula (1) is from 2 to 6, and the hydrophobic amino acid and neutral amino acid of the bridge part are selected from valine, leucine, isoleucine, phenylalanine, tryptophan, glycine, alanine, methionine, serine, threonine, cysteine, tyrosine, asparagine and glutamine.

Since the antimicrobial agent composition comprising the antimicrobial peptide of the invention or the antimicrobial agent composition containing the antimicrobial peptide of the invention has high antimicrobial property, it is useful in preventing bacterial infections and disinfection, sterilization and the like of food materials and the like.

In addition, a recombinant protein can be provided from a polynucleotide (this could be in the form of a DNA segment or RNA segment) which contains a nucleotide sequence coding for the antimicrobial peptide of the invention and/or a nucleotide sequence complementary to said sequence or is substantially constituted from such sequences. This recombinant protein or a degraded product thereof having an antimicrobial activity is useful in preventing bacterial infections and disinfection, sterilization and the like of food materials and the like.

Suitable embodiments of the invention are described in the following. In this connection, in addition to the items particularly mentioned in this specification (e.g., primary structure and chain length of the antimicrobial peptide), other items necessary for carrying out the invention (e.g., general matters such as peptide synthesis, polynucleotide synthesis, and preparation of pharmaceutical agents containing a peptide as the component) can be easily grasped by those skilled in the organic chemistry, biochemistry, genetic engineering, protein engineering, molecular biology, pharmacy, medical science and the like fields. The invention can be carried out easily by those skilled in the art based on the contents disclosed in this specification and the technical common knowledge in said fields. In this connection, each of the amino acids described in the following is expressed by the single letter code in accordance with the nomenclature on amino acids shown by the IUPAC-IUB Guideline (provided that it is in the triple letter code in the Sequence Listing).

The "peptide" as used herein is a term meaning an amino acid polymer having peptide bonds, and the number of amino acid residues contained in the peptide is not restricted. So-called oligopeptide having less that 10 amino acid residues is also included in this specification. In addition, the "polynucleotide" is a term meaning a polymer in which two or more nucleotides are linked through phosphodiester bonds (nucleic acid), which is not restricted by the number of nucleotides. DNA fragments and RNA fragments having various lengths are included in the polynucleotide of the specification.

The inventors of the invention have conducted studies with the aim of providing an antimicrobial peptide having an amino acid sequence which is not restricted to a peptide existing and functioning as an antimicrobial peptide in the natural world and is not based on the conventional developmental approach for antimicrobial peptides. As a result, it was found that an antimicrobial peptide which exerts a high antimicrobial activity and shows a broad antimicrobial spectrum upon Gram-negative bacteria, Gram-positive bacteria and MRSA and the like drug-resistant strains can be realized when the structural characteristics of a bis-type quaternary ammonium salt, namely characteristics in that it has two basic parts in the molecule, structure of the molecule is bilaterally symmetric and its both termini are hydrophobic, are incorporated into the molecular designing of the antimicrobial peptide (Japanese Patent Application No. 2002-344538). The inventors of the invention have continued the studies for the purpose of further improving the antimicrobial property of this antimicrobial peptide and found as a result that this performance is exerted when a moiety of from 1 to 6 hydrophilic amino acid residues is added to one of the termini of this antimicrobial peptide, thereby accomplishing the invention.

The hydrophilic amino acid in the antimicrobial peptide of the invention is selected from arginine, lysine, histidine, aspartic acid, glutamic acid, asparagine and glutamine, which is preferably arginine, lysine or histidine, more preferably arginine or lysine. The n in the formula (1) is an integer of from 1 to 6, preferably an integer of from 1 to 4, and more preferably from 1 to 3.

The number of amino acid residues of the hydrophobic amino acid part in the antimicrobial peptide of the invention is from 2 to 6, preferably 2 or 3, and examples of said amino acids include valine, leucine, isoleucine, phenylalanine, proline, glycine, alanine and methionine, preferably valine, leucine, isoleucine, phenylalanine and alanine, more preferably valine, leucine, isoleucine and alanine. The antimicrobial peptide of the invention has two hydrophobic amino acid parts, wherein the number of amino acid residues of these two parts may be the same or different from each other, preferably the same, and their amino acid sequences may be different sequences, the same sequence or reverse sequences, preferably reverse sequences.

The number of amino acid residues of the basic amino acid part in the antimicrobial peptide of the invention is from 2 to 6, preferably 2 or 3, and examples of said amino acids include lysine, arginine and histidine, preferably lysine and arginine. The antimicrobial peptide of the invention has two basic amino acid parts, wherein the number of amino acid residues of these two parts may be the same or different from each other, preferably the same, and their amino acid sequences may be different sequences, the same sequence or reverse sequences, preferably reverse sequences.

The number of amino acid residues of the bridge part in the antimicrobial peptide of the invention is from 2 to 6, preferably 3 or 4, and a hydrophobic amino acid and a neutral amino acid can be cited as said amino acids, their examples including valine, leucine, isoleucine, phenylalanine, tryptophan, glycine, alanine, methionine, serine, threonine, cysteine, tyrosine, asparagine and glutamine, preferably phenylalanine, tryptophan, serine, threonine or methionine, more preferably tryptophan or methionine.

The antimicrobial peptide of the invention may comprise L-type amino acid residues, D-type amino acid residues or DL-mixed type amino acid residues, but it is antimicrobial peptide are L-amino acids, and it is further desirable that a portion thereof are D-amino acids because of the stability against peptide degrading enzymes. In addition, it is preferably in a straight chain or helical form so long as the antimicrobial activity is not lost, form the viewpoint that a part or all of the amino acid residues can hardly become an antigen. A peptide of such a form hardly forms epitope. From such a point of view, a straight chain is desirable as the peptide to be applied to an antimicrobial agent. In addition, the number of total amino acid residues of the antimicrobial peptide of the invention is from 11 to 30, preferably from 12 to 20.

It is also effective in improving antimicrobial activity to carry out a chemical modification of the N-terminus and/or C-terminus of the antimicrobial peptide of the invention, e.g., to carry out acylation of the N-terminus or amidation of the C-terminus.

As an illustrative example of the antimicrobial peptide of the invention, a peptide substantially constituted from the amino acid sequence represented by SEQ ID NO:1, SEQ ID NO:2 or SEQ ID NO:3 can be cited. Each of these three peptides is constituted by 30 amino acids or less (illustratively from 12 to 14 amino acids), which is suitable for maintaining the straight chain form. In addition, each of them is suitable as the main component (antimicrobial component) of an antimicrobial because of the low immunogenicity.

The antimicrobial peptide of the invention can be easily produced in accordance with a general chemical synthesis method. For example, either of the conventionally known solid phase synthesis method and liquid phase synthesis method may be employed. A solid phase synthesis method in which Boc (t-butyloxycarbonyl) or Fmoc (9-fluorenyl-methoxycarbonyl) is employed as the amino group protective group is suitable.

Regarding the antimicrobial peptide of the invention, a peptide chain having a desired amino acid sequence and a modified (C-terminus amidation or the like) part can be synthesized by a solid phase synthesis method which uses a commercially available peptide synthesizer (e.g., it can be obtained from Applied Biosystems or the like).

Alternatively, the antimicrobial peptide of the invention may be prepared by biosynthesis based on the genetic engineering techniques. This approach is desirable when an antimicrobial peptide having a relatively long chain length is produced. That is, a DNA of a nucleotide sequence (including ATG initiation codon) coding for the amino acid sequence of the desired antimicrobial peptide is synthesized. Thereafter, a recombinant vector having a gene construct for expression use comprising this DNA and various regulatory elements for effecting expression of promoter, a ribosome binding region, a terminator, an enhancer and various cis elements which regulate the expression level) is constructed in response to the host cell.

This recombinant vector is introduced into a predetermined host cell (e.g., a yeast, an insect cell, a plant cell or an animal (mammal) cell) by a general technique, and said host cell or a tissue or individual containing said cell is cultured under predetermined conditions. By doing this, the antimicrobial peptide of interest can be expressed and produced in the cell. Thereafter, the antimicrobial peptide of interest can be obtained by isolating and purifying the antimicrobial peptide from the host cell (in a medium when it is secreted).

The polynucleotide substantially constituted from a nucleotide sequence coding for the antimicrobial peptide of the invention and/or a nucleotide sequence complementary to said sequence can be easily produced (synthesized) by a conventionally known method. That is, a nucleotide sequence corresponding to the amino acid sequence of the antimicrobial peptide is easily determined by selecting codons which correspond to the respective amino acid residues constituting the amino acid sequence of the antimicrobial peptide. Once the nucleotide sequence is determined, a polynucleotide (single-stranded) which corresponds to the desired nucleotide sequence can be easily obtained making use of a DNA synthesizer or the like. Thereafter, the desired double-stranded DNA can be obtained using the thus obtained single-stranded DNA as the template and employing various enzymatic synthesis means.

The polynucleotide provided by the invention may be a form of RNA (mRNA or the like) or a form of DNA. The DNA is provided as a double-stranded or single-stranded form. When it is provided as a single-stranded form, it may be either a code strand (sense strand) or a non-code strand (antisense strand) of a sequence complementary thereto.

The polynucleotide provided by the invention can be used as a material for constructing a recombinant gene (expression cassette) for use in the expression of the antimicrobial peptide of the invention in various host cells.

For example, a recombinant vector having a gene construct for exotic peptide expression use can be constructed using a polynucleotide having a nucleotide sequence coding for the antimicrobial peptide of the invention and various regulatory elements for effecting expression of said amino acid sequence in a host cell (include a promoter, a ribosome binding region, a terminator, an enhancer and various cis elements which regulate the expression level). Constitution of the vector and kinds of regulatory elements to be used in its construction can vary depending on the type of the host cell of interest. The polynucleotide digestion method by various restriction enzymes (restriction) and polynucleotide fragment connection method (ligation) well understood in the field of genetic engineering are employed for the construction of the recombinant vector. These techniques can be easily carried out by making use of various commercially available apparatuses.

In this connection, regarding the method for constructing a recombinant vector and the method for introducing the constructed recombinant vector into a host cell, the methods conventionally carried out in said field can be employed as such and such methods themselves do not particularly characterize the invention, so that their detailed descriptions are omitted.

Since the antimicrobial peptide of the invention has a broad antimicrobial spectrum, it is suitably used as a component of an antimicrobial agent composition (e.g., an antimicrobial agent, a germicidal agent, a disinfectant, an antiseptic, a deodorant or the like).

As the object of the antimicrobial peptide of the invention, bacteria can particularly be exemplified but not particularly limited so far as the antimicrobial effect of the invention is exerted. The object of using the antimicrobial peptide of the invention is not particularly limited, but for example, it is preferably an animal, more preferably an insect or a vertebrate, particularly preferably a mammal, most preferably human. Also, examples of the material with which the antimicrobial peptide of the invention is to be blended include drugs; cosmetics; food; feed; toiletry products; textile products; floors and walls; various supply water; soils; agricultural products and the like. For example, it can be used as an antimicrobial agent or germicidal agent for the treatment of a bacterial infection, disinfection of a wound surface, prevention of an eye trouble, oral cavity washing or for toothpaste use, an antiseptic of medicament, an antiseptic of cosmetics, preservation of contact lenses, an antiseptic or freshness keeping agent of food, a bacteriostatic agent or germicidal agent of kitchen utensils, bathroom utensils, toiletry utensils and the like and a germicidal agent or bacteriostatic agent of the surface of articles of furniture and health apparatus. Also, it can be used as a bacteriostatic agent or germicidal agent for clothes, curtains and the like textile products, a bacteriostatic agent or germicidal agent for floors and walls and further as a germicidal agent or bacteriostatic agent for various supply water such as industrial water, building managing water, bathing water and the like. Also, a deodorant effect can be expected from its antimicrobial or germicidal action. In addition, it can be used as a bacteriostatic agent or germicidal agent in the agricultural field, for example as an agricultural chemical for crops and agricultural materials. It can also be used as a bacteriostatic agent or germicidal agent in the fields of stockbreeding and beekeeping, for example as a stockbreeding feed or as a bacteriostatic agent or germicidal agent for beekeeping boxes. In addition, it can be used as a bacteriostatic agent or germicidal agent in the field of fishing industry, for example for the treatment of fish infected with a bacterium in a fish farm, and sterilization of nets, gloves and the like materials.

There are no limitations regarding the form of an antimicrobial agent composition containing the antimicrobial peptide of the invention. For example, solutions, suspensions, emulsions, aerosols, foams, granules, powders, tablets, capsules, ointments, creams and the like can be exemplified as typical forms of internal preparations and external preparations. In addition, it can also be made into a freeze-dried preparation or granulated preparation for use in the preparation of a drug solution for injection or the like use by dissolving in physiological saline or the like just before the use.

Regarding other carriers namely secondary components (pharmaceutically acceptable) in antimicrobial agent composition and the like preparations containing the antimicrobial peptide of the invention, they can vary in response to the use and form of the antimicrobial agent or the like, and those which are generally used in producing pharmaceutical preparations, such as various packing agents, extenders, binders, moisture providing agents, surface active agents, fillers, pigments, perfumes and the like, can be used.

In this connection, the process itself for preparing various drugs having the aforementioned forms using the antimicrobial peptide of the invention and various carriers as the materials can be carried out in accordance with the conventionally known methods, and such preparation methods themselves do not characterize the invention, so that their detailed descriptions are omitted.

The antimicrobial agent composition containing the antimicrobial peptide of the invention can be used by the method and dose in response to its form and object. For example, solutions can be administered by intravenous, intramuscular, subcutaneous, intradermal or intraperitoneal injection. In addition, tablets and the like solid preparations can be orally administered. The dose in that case can be calculated from the antimicrobial activity of the aimed microorganism. The general dose in this case is for example from 1 to 500 mg/kg body weight, but it can be optionally changed in response to each subject to be administered, and it may be smaller than this range or larger than this range in some cases.

In addition, when used for the purpose of disinfecting (sterilizing) the surface of sanitary china ware or preserving food, this can be carried out by directly spraying a solution containing the antimicrobial peptide of the invention in a relatively large amount (e.g., from 1 to 100 mg/ml)to the surface of the object, or by wiping the surface of the object with cloth or paper wetted with said solution. These are merely examples, and the same forms and using methods of agricultural chemicals, quasi drugs and the like antimicrobial agents and disinfectants by the conventional antimicrobial agents can be applied.

Thus, the invention also provides a sterilization method which comprises the step of applying the aforementioned antimicrobial peptide and a method for inhibiting bacterial growth.

For example, cancer or AIDS patients who are undergoing radiotherapy sometimes cause immunodeficiency as a complication and show serious symptoms by a bacterial infection rather than the cause of the original disease itself. The antimicrobial peptide provided by the invention shows a bacterium-selective antimicrobial action and has no toxicity or low toxicity upon human and the like mammals. Accordingly, the antimicrobial peptide of the invention is useful as a component of antimicrobial agents, so that the antimicrobial agent provided by the invention can be applied safely to the human body.

In the field of regeneration therapy, the antimicrobial peptide of the invention can be used for the purpose of preventing bacterial infection during the culturing of the skin, a bone, respective organ and the like. For example, bacterial infection of a tissue, organ or the like during its culturing can be prevented by adding the antimicrobial peptide of the invention alone, or an antimicrobial agent containing said peptide as one of its components, at an appropriate concentration to the culture medium.

In addition, a polynucleotide coding for the antimicrobial peptide of the invention can be used as a material to be used in a gene therapy of cultured cells or cultured tissues. For example, when a gene (a DNA segment or RNA segment) coding for the antimicrobial peptide of the invention is integrated into an appropriate vector and thereby introduced into the cultured tissues (cells) of interest, it becomes possible to express the antimicrobial peptide of the invention always or during a desired period inside the cultured tissues (cells). Thus, a polynucleotide (a DNA segment or RNA segment) coding for the antimicrobial peptide of the invention is useful as a drug for preventing cultured tissues (cells) from bacterial infection.

A polynucleotide coding for the antimicrobial peptide of the invention can be used as a material to be used in so-called gene therapy. For example, when a gene (a DNA segment or RNA segment) coding for the antimicrobial peptide of the invention is integrated into an appropriate vector and thereby introduced into the region of interest, it becomes possible to express the antimicrobial peptide of the invention always in the living body (cells). Thus, a polynucleotide (a DNA segment or RNA segment) coding for the antimicrobial peptide of the invention is useful as a drug for the aforementioned patients and the like in preventing or treating bacterial infection.

The invention is described further in detail based on the examples described in the following, though not intended to limit the invention to such examples.

EXAMPLE 1

Synthesis of Antimicrobial Peptides:

A total of 4 peptides of samples 1 to 3 and comparative example 1 were produced using a peptide synthesizer described in the following. Amino acid sequences of these peptides are shown below.

| Sample name | Amino acid sequence | | The number of total amino acid residues |
|---|---|---|---|
| Sample 1 | RLLRKWWWKRLL | (SEQ ID NO:1) | 12 |
| Sample 2 | RRLLRKWWWKRLL | (SEQ ID NO:2) | 13 |
| Sample 3 | RRRLLRKWWWKRLL | (SEQ ID NO:3) | 14 |
| Comp. Ex. 1 | LLRKWWWKRLL | (SEQ ID NO:4) | 11 |

Each of the aforementioned peptides (cf. Sequence Listing for respective amino acid sequences) was synthesized by a solid phase synthesis method (Fmoc method) in accordance with FastMoc™ protocol using a commercially available peptide synthesizer (ABI 433A peptide synthesizer (mfd. by Applied Biosystems)). In this case, HATU (mfd. by Applied Biosystems) was used as the condensing agent, and the resin and amino acids used in the solid phase synthesis were purchased from NOVA Biochem. In addition, among the Fmoc-amino acids used, tert-butoxycarbonyl (Boc) was used as the protecting group of Lys, and triphenylmethyl (Trt) as the protecting group of His and pentamethylchroman-6-sulfonyl (Pmc) as the protecting group of Arg.

In the case of the amidation of the amino acid sequence C-terminus, "Fmoc-PAL-Polyethylene (PEG-PS) resin" was used as the solid phase carrier.

Thus, each synthetic peptide of the intended chain length was obtained by elongating the peptide chain from the Fmoc-amino acid binding to the resin, through the repetition of deprotection reaction and condensation reaction in accordance with the synthesis program of the aforementioned peptide synthesizer. Illustratively, this was effected by repeating an operation in which Fmoc as the amino protecting group of amino acid is digested and removed using 20% piperidine/dimethylformamide (DMF) (peptide synthesis grade, mfd. By Kanto Kagaku) and washed with DMF, and then 3 eq of each Fmoc-amino acid(—OH) is allowed to undergo the reaction and washed with DMF. After completion of all of the peptide chain elongation reactions, the Fmoc group was digested with 20% piperidine/DMF, and the aforementioned reaction product was washed with DMF and methanol in that order. Regarding deprotection of side chain or release of peptide from the resin, 5 ml of 82.5% trifluoroacetic acid (TFA hereinafter) (TFA:1,2-ethandithiol:m-cresole:thioanisole:water=82.5:2.5:5:5:5) (all available from Wako Pure Chemical Industries) was added and allowed to undergo the reaction at room temperature for 3 hours, or 10 ml of 70% TFA (TFA:trimethylsilyl bromide:thioanisole:1,2-ethandithiol:m-cresole=70:13:11:5:1) (all available from Wako Pure Chemical Industries) was added and allowed to undergo the reaction at 0° C. for 1 hour in an atmosphere of nitrogen. The resin was removed, and the residue was precipitated in diethyl ether (mfd. by Kanto Kagaku) and centrifuged (3,000 rpm, 4° C., 3 min) to remove the ether layer. By repeating this 3 times, the peptide was washed. After finally removing the ether layer, the peptide was air-dried and dissolved in pure water. A sample which did not dissolve in pure water was dissolved in 30% or less ethanol/pure water. Thereafter, each sample was freeze-dried.

The thus obtained peptide precipitate was vacuum-dried and purified using a high performance liquid chromatography.

Illustratively, a pre-column (mfd. by Guard-Pak, product name Deltapak C18 A300) and a C18 reverse phase column (DAISOPAK SP-120-5-ODS-AP, 20 mm I.D.×250 mm (mfd. by DAISO)) were used, and a mixed solution of 0.1% trifluoroacetic acid aqueous solution and 0.1% trifluoroacetic acid acetonitrile solution was used as the eluent. That is, 40 to 50 minutes of separation purification was carried out using the aforementioned columns at a flow rate of 7.0 ml/min, while periodically increasing ratio of the trifluoroacetic acid acetonitrile solution contained in the eluent (setting a density gradient of from 10% to 80% by volume ratio). In this case, the peptide eluted from the reverse phase column was detected with an ultraviolet ray detector (wavelength: 220 nm).

Also, molecular weight of each of the eluted peptides was determined using a KRATOS mass spectrometer KOMPACT MALDI III (mfd. by Shimadzu) based on MALDI-TOF/MS (matrix-assisted laser desorption time of flight mass spectrometry). As a result, it was confirmed that the peptides of interest were synthesized and purified.

EXAMPLE 2

Antimicrobial Activity of Synthetic Peptides:

Antimicrobial activity (minimum inhibitory concentration: MIC) of the samples 1 to 3 produced in Example 1 and the peptide of comparative example 1 upon the Gram-negative bacteria and Gram-positive bacteria shown below was calculated by a liquid medium dilution method using a 96 well microplate.

Bacteria Tested:
Gram-Positive Bacteria:
*Staphylococcus aureus* IFO 12732
*Staphylococcus aureus* COL1 (MRSA)
*Bacillus cereus* IFO 3001
*Bacillus subtilis* ATCC 6633
*Micrococcus luteus* IFO 12708
Gram-Negative Bacteria:
*Escherichia coli* IFO 12713
*Escherichia coli* 0157:H7 sakai
*Klebsiella pneumoniae* ATCC 4352
*Pseudomonas aeruginosa* ATCC 10145

That is, each sample was diluted with a liquid bouillon medium (mfd. by DIFCO, product name "NUTRIENT BROTH Dehydrated") to a peptide concentration of 500, 250, 125, 62.5, 31.3, 15.6, 7.8, 3.9, 1.9, 1.0 or 0.5 μM and dispensed in 150 μl portions into a 96 well microplate. On the other hand, a cell suspension (about $2 \times 10^6$ cells/ml) prepared by statically culturing each strain at 37° C. for 18 hours in LB Broth, Lennox (mfd. by DIFCO) was inoculated into each well of the 96 well microplate in an amount equivalent to that of the drug solution (the aforementioned peptide-containing bouillon medium). After the inoculation, the culturing was started in an incubator of 37° C., and the presence of bacterial growth was examined based on the turbidity after 24 hours. The minimum peptide concentration by which increase in the turbidity due to bacterial growth was not observed at the time of the measurement was defined as the MIC in this Example.

Antimicrobial activities (minimum inhibitory concentration: MIC) of the respective samples and comparative sample based on this antimicrobial test are shown in Table 1.

TABLE 1

| | MIC (μg/ml) | | | |
|---|---|---|---|---|
| | Sample 1 | Sample 2 | Sample 3 | Comparative Example 1 |
| Gram-positive bacteria | | | | |
| Staphylococcus aureus IFO 12732 | 1.95 | 1.95 | 1.95 | 1.95 |
| Staphylococcus aureus COL1 (MRSA) | 15.6 | 15.6 | 15.6 | 31.3 |
| Bacillus cereus IFO 3001 | 62.5 | 62.5 | 62.5 | 62.5 |
| Bacillus subtilis ATCC 6633 | 1.95 | 1.95 | 1.95 | 0.98 |
| Micrococcus luteus IFO 12708 | 3.9 | 3.9 | 7.8 | 7.8 |
| Gram-negative bacteria | | | | |
| Escherichia coli IFO 12713 | 15.6 | 7.8 | 15.6 | 62.5 |
| Escherichia coli O157: H7 (sakai) | 15.6 | 7.8 | 15.6 | 31.3 |
| Klebsiella pneumoniae ATCC 4352 | 7.8 | 3.9 | 3.9 | 15.6 |
| Salmonella enteritidis IFO 3313 | 3.9 | 3.9 | 3.9 | 15.6 |
| Pseudomonas aeruginosa ATCC 10145 | 15.6 | 15.6 | 15.6 | 62.5 |

As is evident from the results shown in Table 1, the peptides of the invention (samples 1 to 3) kept almost the same high antimicrobial activity upon Gram-positive bacteria in comparison with the symmetric antimicrobial peptide of the comparative control (SEQ ID NO:4), while showing 2 to 8 times higher excellent antimicrobial activity than that of the comparative example 1 upon Gram-negative bacteria.

From the results shown in Table 1, it is evident that the antimicrobial peptide of the invention has excellent antimicrobial activity and broad antimicrobial spectrum upon Gram-negative, Gram-positive and drug-resistant strains.

Thus, illustrative examples of the invention have been described in detail in the foregoing, but these are merely an illustration and do not limit the claims. Various modifications and changes of the illustrative examples exemplified in the foregoing are included in the techniques described in the claims.

In addition, the technical elements described in this specification exert their technical availability, alone or by various combinations, so that they are not limited to the combinations described in the claims. Also, the techniques exemplified in this specification can attain two or more objects simultaneously, and attainment of one object among them has by itself has a technical availability.

Sequence Listing Free Text

SEQ ID NO:1 A designed antimicrobial peptide.

SEQ ID NO:2 A designed antimicrobial peptide.

SEQ ID NO:3 A designed antimicrobial peptide.

SEQ ID NO:4 A designed antimicrobial peptide.

This application is based on Japanese patent application No. 2003-359002 filed Oct. 20, 2003, the entire contents thereof being hereby incorporated by reference.

What is claimed is:

1. An antimicrobial peptide which has the amino acid sequence described in SEQ ID NO:1, SEQ ID NO:2 or SEQ ID NO:3.

2. An antimicrobial agent composition which contains the antimicrobial peptide described in claim 1 and a carrier.

3. A sterilization method which comprises the step of applying the antimicrobial peptide described in claim 1.

* * * * *